US005457214A

United States Patent [19]

[11] Patent Number: 5,457,214
[45] Date of Patent: Oct. 10, 1995

O'Donnell

[54] RECOVERY OF ERYTHORBATES FROM PHOTOGRAPHIC SOLUTIONS

[75] Inventor: Alvin J. O'Donnell, New York, N.Y.

[73] Assignee: Pfizer Inc., New York, N.Y.

[21] Appl. No.: 326,146

[22] Filed: Oct. 19, 1994

Related U.S. Application Data

[63] Continuation of Ser. No. 998,697, Dec. 30, 1992, abandoned.

[51] Int. Cl.[6] .................................................. C07D 307/28
[52] U.S. Cl. .................................................................. 549/315
[58] Field of Search ............................................... 549/315

[56] References Cited

U.S. PATENT DOCUMENTS

| | | | |
|---|---|---|---|
| 2,517,276 | 8/1950 | Bassford | 549/318 |
| 4,159,990 | 7/1979 | Andrews | 549/315 |
| 4,212,988 | 7/1980 | Andrews | 549/315 |
| 4,778,902 | 10/1988 | Fujiwar | 549/315 |

*Primary Examiner*—C. Warren Ivy
*Assistant Examiner*—Raymond Covington
*Attorney, Agent, or Firm*—Peter C. Richardson; Cregg C. Benson; Robert F. Sheyka

[57] ABSTRACT

The present invention is directed to a method for the recovery of erythorbates from photographic solutions. In the disclosed method, the photographic solution is first acidified by passing it over an acidic cation exchange resin and the resultant solution is then passed over a weakly basic anion exchange resin.

19 Claims, No Drawings

RECOVERY OF ERYTHORBATES FROM PHOTOGRAPHIC SOLUTIONS

This is a continuation, of application Ser. No. 07/998,697, filed on Dec. 30, 1992, now abandoned.

BACKGROUND OF INVENTION

The present invention is directed to a process for the recovery of erythorbate values from spent photographic solutions.

Typically, the processing of silver halide emulsions begins with the exposure of the emulsion to radiation to which the emulsion is sensitized to produce a latent image in the silver halide grains of the emulsion. The latent image is developed by immersion of the exposed emulsion in an aqueous developing solution usually containing a reducing agent which functions as a developer. An example of such a reducing agent is hydroquimone.

Other developing agents which have been used are derivatives of ascorbic acid, i.e. erythorbic acid or erythorbates. The use of these derivatives as developers are discussed in a number of United States Patents.

U.S. Pat. No. 3,942,985 refers to a developer composition comprised of at least one iron chelate developer and ascorbic acid, or specific derivatives thereof.

U.S. Pat. No. 2,688,549 refers to a photographic composition which uses ascorbic acid, and specified derivatives thereof, together with 3-pyrazolidone compounds as a developing medium.

U.S. Pat. No. 3,022,168 refers to photographic developer compositions which use ascorbic acid as a developer. The compositions are at a pH of from about 8.5 to about 9.

U.S. Pat. No. 5,098,819 refers to a photographic composition containing ascorbic acid; specified derivatives thereof, a sulfite, an alkali metal carbonate and a 3 pyrazolidone compound. The composition is at a pH of from 9.75 to 10.6.

SUMMARY OF THE INVENTION

In one embodiment the present invention is directed to a process for the substantial purification of the erythorbic values from a spent photographic solution containing said values comprising:

(a) acidifying a spent photographic solution containing said values by passing said solution over an acidic cation exchange resin;

(b) passing the acidified solution of (a) over a weakly basic anion exchange resin.

In a further embodiment, the process further comprises the step of (c) neutralizing the solution of (b) with a suitable base.

In a further embodiment, the process further comprises the step of recovering the erythorbic values from step (c).

Preferred is the process wherein said recovery is by crystallization.

Also preferred is a process wherein said crystallization is by the addition of a water miscible solvent.

Especially preferred is the process wherein said water miscible solvent is selected from the group consisting of aldehydes, ketones, and $C_1$–$C_6$ alkanols with an especially preferred alkanol being methanol.

Preferred is the process wherein said erythorbic values are erythorbates.

Also preferred is the process wherein said erythorbic values are erythorbic acid.

Preferred especially is the process wherein said acidic cation exchange resin is a sulfonic acid resin.

Also especially preferred is the process wherein said weakly basic anion exchange resin is an amine resin.

Preferred is the process wherein said base of step (c) is selected from the group consisting of alkali metal hydroxides and alkali metal carbonates; and mixtures thereof with an especially preferred alkali metal hydroxide being potassium hydroxide.

Further preferred is the process wherein said spent photographic solution is at a pH of from about 7.5 to about 11.0.

DETAILED DESCRIPTION OF THE INVENTION

The process of the present invention is directed to the recovery of erythorbate values from spent photographic solutions. The photographic solution may contain erythorbic acid or salts thereof, for example, potassium erythorbate, as the sole developing agent. The photographic solution may contain alkyl esters of erythorbic acid, for example, methyl erythorbate, as the developing agent. The photographic solution may also contain any combination of erythorbic acid, salts thereof, or esters thereof.

The erythorbate values may be present as the sole developing agent in photographic compositions or may be in combination with other co-developing agents. Non limiting example of such other agents include alkali metal carbonates, for example, sodium carbonate and potassium carbonate; 3- pyrazolidone compounds such as phenidone (1 phenyl-3-pyrazolidone); alkali metal sulfites such as, for example, sodium sulfite; metal chelating agents such as, for example, sodium ethylenediaminetetraacetic acid (EDTA); bromides such as, for example, potassium or sodium bromide; and organic antifogging agents such as tetrazoles. A typical photographic solution will contain any combination of the above listed components.

During the development of an image on a photographic medium, various components of the medium, notably the erythorbates, are converted to oxalic acids. Depending on the degree of decomposition, the spent photographic solution is normally at a pH of from about 7.5 to about 13.

In the first step of the process of the present invention, a spent photographic solution is acidified by passing over an acidic cation exchange resin, for example, a sulfonic acid type resin. An example of such a resin is Ambedite IRC-200 (Rohm and Haas, Philadelphia, Pa.) which is regenerated or activated with a mineral acid such as hydrochloric acid, sulfuric acid, phosphoric acid or nitric acid.

The acidified solution generated by passage through the acidic cation exchange resin is then passed over a weakly basic anion exchange resin, for example, an amine type resin. An example of such a resin is IRA-93 (Rohm and Haas, Philadelphia, Pa.). The resin may be activated by use of, for example, sodium hydroxide, potassium hydroxide or other bases, such as, for example, ammonium hydroxide.

After passage of the photographic solution over the weakly basic anion exchange resin, the solution may then be neutralized with an appropriate base. Non limiting examples of suitable bases which may be used are alkali metal hydroxides such as, for example, sodium hydroxide or potassium hydroxide, and alkali metal carbonates such as, for example, sodium carbonate or potassium carbonate. An especially preferred bases are sodium hydroxide and potassium hydroxide.

After the photographic solution has been neutralized, it may be used as is to reformulate fresh photographic developer solution.

Alternately, the solution may be concentrated by, for example, vacuum distillation. After concentration, the erythorbate values may be crystallized. Crystallization may be accomplished by cooling or by the addition of a water miscible solvent. Non limiting examples of water miscible solvents include aldehydes, ketones and lower ($C_1$–$C_6$) alkanols, for example, methanol.

Having described the invention in general terms, reference is now made to specific examples. It is to be understood that these examples are not meant to limit the present invention, the scope of which is determined by the appended claims.

EXAMPLE 1

One liter of spent photographic developing solution containing the equivalent of approximately 110 g. of erythorbic acid was acidified by passing it over an ion exchange column containing a cation exchange resin of the sulfonic acid type (e.g. Amberlite IRC-200) which had previously been put in the hydrogen form.

A portion of the resulting solution was then passed over a second ion-exchange column containing a weak basic anion exchange resin of the amine type (e.g. Ambedite IRA 93) which had previously been put in the free-base form.

A portion of that resulting solution was then neutralized with sodium hydroxide, concentrated by vacuum distillation and the sodium salt of erythorbic acid crystallized via the addition of methanol. After filtration, washing and drying the isolated salt exhibited a purity of 99.8% as determined by iodometric titration.

I claim:

1. A process for the substantial purification of the erythorbic values from a spent photographic solution containing said values, said spent photographic solution containing erythorbic decomposition products in the form of oxalic acids, comprising:

(a) acidifying a spent photographic solution containing said values by passing said solution over an acidic cation exchange resin;

(b) passing the acidified solution of (a) over a weakly basic anion exchange resin, to remove said oxalic acids.

2. A process according to claim 1 further comprising the step of (c) neutralizing the solution of (b) with a suitable base.

3. A process according to claim 1 further comprising the step of recovering the erythorbic values from step (b).

4. A process according to claim 2 further comprising the step of recovering the erythorbic values from step (c).

5. A process according to claim 3 wherein said recovery is by crystallization.

6. A process according to claim 4 wherein said recovery is by crystallization.

7. A process according to claim B wherein said crystallization is by the addition of a water miscible solvent.

8. A process according to claim 6 wherein said crystallization is by the addition of a water miscible solvent.

9. A process according to claim 7 when said water miscible solvent is selected from the group consisting of aldehydes, ketones, and $C_1$–$C_6$ alkanols.

10. A process according to claim 8 wherein said water miscible solvent is selected from the group consisting of aldehydes, ketones and $C_1$–$C_6$ alkanols.

11. A process according to claim 9 where said alkanol is methanol.

12. A process according to claim 10 wherein said alkanol is methanol.

13. A process according to claim 2 wherein said erythorbic values are erythorbic acid.

14. A process according to claim 1 wherein said erythorbic values are erythorbates.

15. A process according to claim 1 wherein said acidic cation exchange resin is a sulfonic acid resin.

16. A process according to claim 1 wherein said weakly basic anion exchange resin is an amine resin.

17. A process according to claim 2 wherein said base of (c) is selected from the group consisting of alkali metal hydroxides and alkali metal carbonates; and mixtures thereof.

18. A process according to claim 17 wherein said alkali metal hydroxide is selected from the group consisting of sodium hydroxide and potassium hydroxide.

19. A process according to claim 1 wherein said spent photographic solution is at a pH of from about 7.5 to about 11.0.

* * * * *